(12) United States Patent
Lana et al.

(10) Patent No.: US 11,913,392 B2
(45) Date of Patent: Feb. 27, 2024

(54) METHOD, APPARATUS, AND SYSTEM FOR CONTROLLING NATURAL GAS ENGINE OPERATION BASED ON FUEL PROPERTIES

(71) Applicant: Cummins Inc., Columbus, IN (US)

(72) Inventors: Carlos Alcides Lana, Columbus, IN (US); Yilun Liu, Columbus, IN (US); Philipe F. Saad, Columbus, IN (US); Ganesh Raghunath, Columbus, IN (US)

(73) Assignee: Cummins Inc., Columbus, IN (US)

( * ) Notice: Subject to any disclaimer, the term of this patent is extended or adjusted under 35 U.S.C. 154(b) by 52 days.

(21) Appl. No.: 17/449,004

(22) Filed: Sep. 27, 2021

(65) Prior Publication Data

US 2022/0010740 A1    Jan. 13, 2022

Related U.S. Application Data

(63) Continuation of application No. PCT/US2020/030629, filed on Apr. 30, 2020.
(Continued)

(51) Int. Cl.
*F02D 41/00* (2006.01)
*F02D 41/14* (2006.01)
(Continued)

(52) U.S. Cl.
CPC ....... *F02D 41/0027* (2013.01); *F02D 19/029* (2013.01); *F02D 41/1441* (2013.01);
(Continued)

(58) Field of Classification Search
CPC .............. F02D 19/029; F02D 41/0027; F02D 41/1441; F02D 41/1451; F02D 41/1454; F02D 41/2454
See application file for complete search history.

(56) References Cited

U.S. PATENT DOCUMENTS 6,237,575 B1    5/2001   Lampert et al.
6,612,269 B2    9/2003   Heffel et al.
(Continued)

FOREIGN PATENT DOCUMENTS

DE    19622105 A1    12/1996
JP    2003148187 A  *  5/2003
(Continued)

OTHER PUBLICATIONS

Search Report and Written Opinion, PCT Appln. No. PCT/US20/30629, dated Aug. 4, 2020, 9 pgs.
(Continued)

*Primary Examiner* — Hung Q Nguyen
*Assistant Examiner* — Mark L. Greene
(74) *Attorney, Agent, or Firm* — Taft, Stettinius & Hollister LLP

(57) ABSTRACT

A method, system, and apparatus use infrared spectrometry onboard an internal combustion engine running on a natural gas fuel to detect characteristics of the fuel. At a site having a plurality of natural gas engines, detection of natural gas fuel components and concentrations of the components also is conducted at the site upstream of the point of intake of the natural gas fuel to one or more of the engines. Operating parameters of the engine or a plurality of the engines may be controlled on the basis of the detected composition of the natural gas fuel.

18 Claims, 6 Drawing Sheets

Related U.S. Application Data

(60) Provisional application No. 62/842,144, filed on May 2, 2019.

(51) Int. Cl.
   F02D 41/24     (2006.01)
   F02D 19/02     (2006.01)

(52) U.S. Cl.
   CPC ..... F02D 41/1451 (2013.01); F02D 41/1454 (2013.01); F02D 41/2454 (2013.01)

(56) References Cited

U.S. PATENT DOCUMENTS

| | | | |
|---|---|---|---|
| 6,912,480 B2 | 6/2005 | Black | |
| 7,091,509 B2 | 8/2006 | Rahmouni et al. | |
| 8,903,662 B2* | 12/2014 | Bats | G01N 9/36 |
| | | | 702/182 |
| 9,291,610 B2 | 3/2016 | Zelepouga et al. | |
| 9,932,910 B2 | 4/2018 | Hunter | |
| 10,669,954 B2* | 6/2020 | King | F02M 21/06 |
| 2017/0145965 A1 | 5/2017 | Singh et al. | |
| 2017/0276655 A1 | 9/2017 | Li | |
| 2018/0163666 A1* | 6/2018 | Mohara | G01N 33/0016 |

FOREIGN PATENT DOCUMENTS

| | | |
|---|---|---|
| JP | 2005256764 A * | 9/2005 |
| JP | 2016205317 A | 12/2016 |
| WO | WO-2017184492 A1 * | 10/2017 |
| WO | 2018059834 | 4/2018 |
| WO | 2018208326 | 11/2018 |

OTHER PUBLICATIONS

European Extended Search Report, EP Appln. No. 20798760.3, dated Nov. 11, 2022 8 pgs.

* cited by examiner

METHOD, APPARATUS, AND SYSTEM FOR CONTROLLING NATURAL GAS ENGINE OPERATION BASED ON FUEL PROPERTIES

CROSS-REFERENCE TO RELATED APPLICATIONS

This is a continuation of International Patent Application Serial No. PCT/US20/30629, filed Apr. 30, 2020 which claims priority to and the benefit of U.S. Provisional Patent Application No. 62/842,144 filed May 2, 2019, the entire disclosures of which are incorporated herein by reference.

TECHNICAL FIELD

The technical field relates to internal combustion engines. More particularly, the invention relates to internal combustion engines that may burn natural gas as a fuel, and to apparatus, systems, and methods relating to controlling engine operation parameters based on detection of properties of the natural gas fuel.

BACKGROUND

Natural gas is a naturally occurring hydrocarbon mixture containing primarily methane. The methane content significantly contributes to the combustion characteristics of natural gas. Natural gas also contains smaller percentages of other hydrocarbons, carbon dioxide, nitrogen, water vapor, and hydrogen sulfide. The percentage composition of the component gases of natural gas can vary widely, resulting in varying combustion characteristics. In particular, natural gas from different wellhead sources may vary widely depending upon the geographic location of the source.

Precise measurement of natural gas composition is needed in order to optimize the control of engine operating parameters such as optimizing the air-to-fuel ratio for a given set of engine operating conditions or parameters. However, current gas composition measuring equipment and techniques have drawbacks. Some sensors having superior capabilities for detecting the largest number of different components within the gas mixture, or detecting with highest accuracy the relative concentrations of the components in the gas mixture, are expensive, pose hazards when operated in some onboard engine environments, and/or have slow response times resulting in delays in providing feedback needed to optimize engine operation. For example, a conventional method using zirconia-based chemical oxygen sensors may be hazardous to use due to the possibility of combusting the air-fuel mixture due to the elevated temperatures required for their operation.

An example of a known onboard sensor for detecting characteristics of a natural gas used as a fuel in an internal combustion engine is found in Hunter, et al., U.S. Pat. No. 9,932,910 B2 issued Apr. 3, 2018, the contents of which are incorporated by reference herein in their entirety. However, there remains a continuing need for improved apparatus and methods to detect with more accuracy and speed the components and composition of a natural gas fuel, particularly in applications such as internal combustion engines fueled by natural gas in power generation facilities.

SUMMARY

Various embodiments of the disclosure relate to a method, and related apparatuses such as engines, controls, and systems, for detecting components of natural gas fuel used in an internal combustion engine system, and detecting concentrations of such components within the natural gas fuel. Disclosed are a method and related apparatus which may use mid-infrared spectrometry onboard an internal combustion engine running on a natural gas fuel to detect characteristics of the fuel. In a power generation site having a plurality of internal combustion engines, preferably the method and apparatus include detection of natural gas fuel components and concentrations of the components at the site, and upstream of the point of intake of the natural gas fuel to one or more of the internal combustion engines, referred to herein as onsite detection. Onsite detection may preferably include use of Fourier transform infrared spectrometry to detect components and concentrations of natural gas fuel being fed to the plurality of engines. Operating parameters of the engine or a plurality of the engines may be controlled on the basis of the detected composition of the natural gas fuel. The controlled operating parameters may include air-to-fuel ratios, optimum spark timing, cam phasing, stoichiometric (lean/rich) limits, and other engine control parameters to optimize engine performance and fuel efficiency of power generation.

While multiple embodiments are disclosed, still other embodiments of the present invention will become apparent to those skilled in the art from the following detailed description, which shows and describes illustrative embodiments of the invention.

Figure 1:
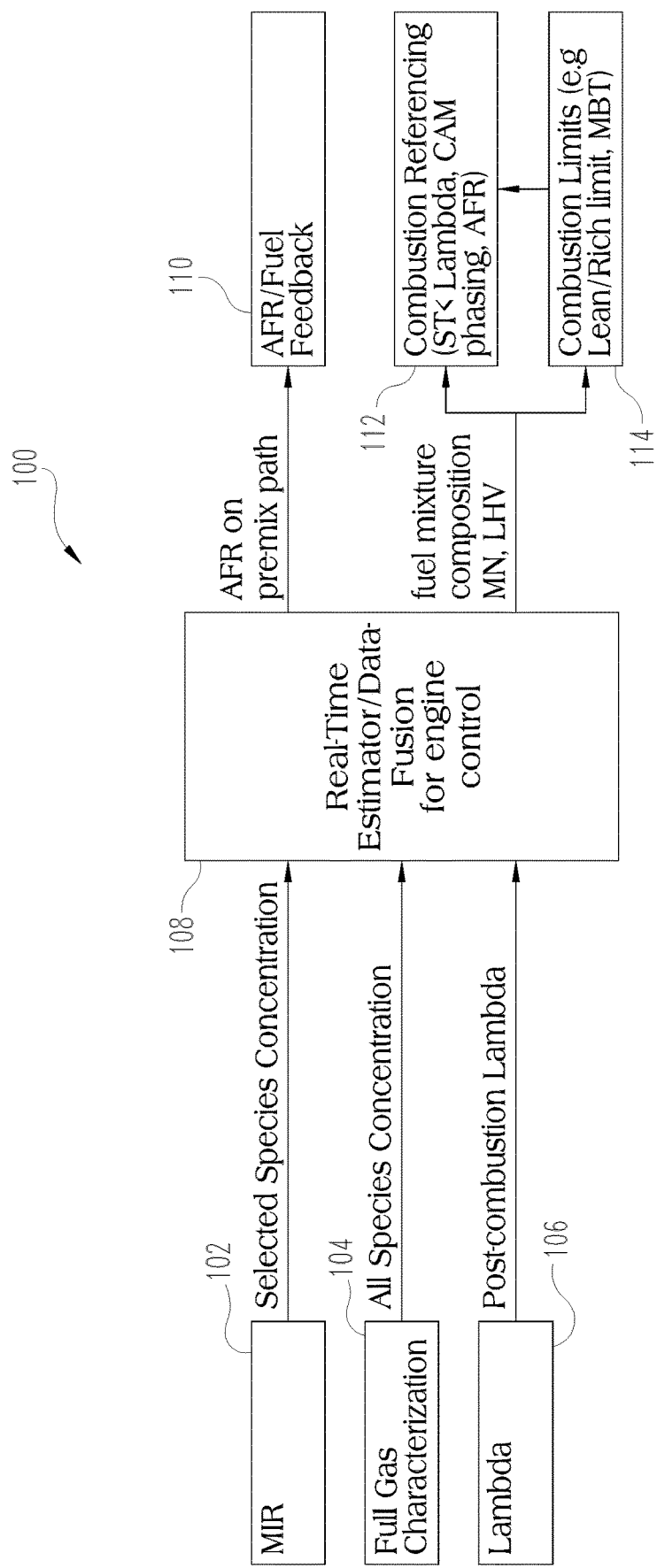
FIG. 1 is a schematic diagram representing an engine control system or method according to some embodiments.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

It is useful to detect components comprised in a natural gas, which typically includes a mixture of methane, other hydrocarbons, carbon dioxide, nitrogen, water vapor, and hydrogen sulfide. A useful characteristic to measure in a natural gas fuel is a methane number (MN), which may indicate a tendency of a fuel to cause engine knock upon combustion of the fuel. MN calculation requires determination of all fuel constituents that comprise a substantial proportion of the fuel contents. The relative concentration levels also are useful to making an MN calculation. Also, the relative concentration levels are useful for determining air to fuel ratios (AFR) in real-time operating conditions in a natural gas-fueled engine. Thus, a preferred method and system for detection may include determining the relative quantities of such components, such as determining a concentration of each component detected in the natural gas by percentage of volume or other applicable unit expressing relative proportions of component gasses. Preferably the determination is made in a manner that most accurately represents the components and concentrations as they exist in real-time operating conditions within the combustion cylinder. The invention in general relates to use of improved detection methods and systems that employ Fourier transform infrared (FTIR) analyzers and mid-infrared (MIR) analyzers to provide more accurate MN and AFR determinations.

FTIR and MIR analyzers emit different wavelengths of infrared light to measure the different species of compounds present in a gas sample based on their signature peaks. Using the same broadband detector, multiple IR laser emitters may be used at the wavelengths of the different species to detect each signature peak. The amplitude of each peak can be used to estimate the concentration of selected constituents. Solid state quantum cascade lasers (QCL) may be used, which emit in the mid- to far-IR portion of the spectrum. Here, the laser emission is achieved through the use of intersubband transitions in a repeated stack of semiconductor multiple quantum well heterostructures. Since such a laser does not use recombination of electron-hole pairs which are typical in interband semiconductor lasers, there is not a need for use of pumps to create recombination across the material band gap. The wavelength is tuned due to heating of the emitter by the pulse which modifies the refractive index of the emitter lens. Such QCLs typically consume very little power (~25 mWh), are robust to dispersion and other noise factors such as vibrations. On the detector side, a tuning fork based detector is used specific for each constituent of the gas species where the QCL intensity is modulated by the gas concentration and the quantum detector signal (tuning fork) is proportional to the QCL intensity. This enables fast sampling of the flowing gas in the gas chamber which can be used for real-time measurements of composition.

In a specific embodiment of such IR sensors, there exists an intake and exhaust valve through which the intake air and fuel is fed into a gas chamber. A laser emitter emits laser lights of a certain wavelength correlating to a specific species in the intake charge in short pulses through a window into the gas chamber and this light is detected by the broadband laser detector on the opposite side of the chamber. This process is repeated for as many components of the intake gas are needed to be measured. Based on the measurement of selected hydrocarbons and oxygen content, the air-fuel ratio (AFR) is calculated and is used to for combustion controls. Measuring the AFR at intake is more robust and responsive than measuring oxygen downstream and estimating the intake AFR and setting engine controls based on the measurement.

In some embodiments, the invention relates to a method of operating or controls of an internal combustion engine system. Shown in FIG. 1 is a control method or system 100 for controlling operation of an engine system. The engine system includes at least one internal combustion engine that operates by combusting a natural gas fuel. The engine system may also optionally comprise at least one internal combustion engine that combusts other fuels such as gasoline or diesel fuels. The control system 100 includes steps and apparatus for detecting characteristics of natural gas fuel.

The detection may be conducted in one or more stages. A first stage of detection, represented as full gas characterization in FIG. 1, may be an onsite stage wherein at least one characteristic of fuel to be supplied to an internal combustion engine are detected at at least one position upstream of the intake charge of the internal combustion engine. Onsite detection may comprise use of a first analyzer or sensor device capable of detecting one or more characteristics of the natural gas. The determined characteristic may be in the nature of identifying one or more of component species present in the natural gas, and/or of detecting relative concentrations of one or more identified component species. Onsite detection may be conducted at a position upstream of a fuel inlet of a natural gas engine of the system.

The onsite analyzer or sensor device may include a Fourier transform infrared (FTIR) analyzer 104. The FTIR analyzer 104 may comprise a laser emitter that emits a laser beam and an IR detector that measures the absorption spectrum of components of the natural gas fuel in a test chamber located in the optical path of the laser beam. The species present in the gas mixture may be identified based on the signature of the spectrum received by the detector. The identities of the detected species may be recorded. The FTIR analyzer 104 may preferably be configured to detect or estimate relative concentrations of the respective species that were identified in the natural gas fuel. Values for the detected concentrations of the identified species may be recorded. The detected characteristics and/or values for the characteristics may be provided as an input, or via an input or input device, to a processor of the engine system.

An FTIR analyzer 104 typically has sensitivity capabilities allowing the analyzer to detect presence of a large number of different species of components in a given sample of a gaseous fuel, providing the benefit of identification of a greater range of species as compared to other types of analyzers. Thus, it may be preferable to use the FTIR analyzer to detect two or more, or a plurality, of the components of the natural gas fuel. However, an FTIR analyzer 104 typically has characteristics making onboard installation impractical, such as relatively large size. High cost of FTIR analyzer equipment makes such impractical to incorporate for onboard detection FTIR analyzer processes require relatively long detection time periods making the processes unsuitable for onboard detection functions due to need for shorter feedback times in onboard applications. FTIR analyzers are sensitive to temperature and vibrations in a manner that renders them less suitable for onboard installation than other sensor types.

Thus the inventors have developed a combination of detection stages using different detecting devices that optimizes sensor and analyzer use based on characteristics of sensors and analyzers that may be appropriate for use in different settings.

In embodiments of the invention, a second stage of detection is an onboard stage wherein at least one second analyzer or sensor positioned onboard the at least one internal combustion engine detects at least one characteristic of the natural gas supplied to the engine for combustion. In FIG. 1, the onboard detection stage step and apparatus is represented by the mid-infrared (MIR) analyzer 102. In an embodiment, the onboard detection may be conducted in the gaseous fuel supplied to the engine at a position downstream of the fuel inlet of the engine. In an embodiment, the onboard detection may be conducted at one or more positions upstream of the engine block of the internal combustion engine. In an embodiment, the onboard detection may be conducted at a position upstream of the engine block and downstream of a point of introduction of charge air into the natural gas fuel.

In an embodiment, the engine system may thus comprise an analyzer or sensor 102 positioned onboard at least one engine and capable of detecting selected components of the natural gas fuel in the intake charge of the engine. The analyzer may comprise at least one mid-infrared (MIR) analyzer, comprising an MIR laser emitter that emits a laser beam and an IR detector that measures the absorption spectrum of components of the fuel in a test chamber located in the optical path of the laser beam. A characteristic of the fuel in the nature of a detected species of one or more of the components present in the gas mixture can therefore be identified based on the signature of the spectrum received by the detector, and recorded. The MIR analyzer may preferably be configured to detect or estimate a concentration of one or more of the respective species that are identified in the natural gas fuel. Characteristics and/or values for the one or more detected characteristics, such as concentrations of the identified species, may be recorded and provided or otherwise communicated via an input or input device to a processor of the system. Because natural gas fuel characteristics are not static, with batches of gaseous fuel fluctuating over time in species and in concentration levels of the respective species, the embodiments may employ onboard MIR analyzers to detect species and concentration levels at a time prior to and as close as possible to the moment of combustion in the engine block.

An MIR analyzer typically has less capability than an FTIR analyzer to detect the presence of a large number of different species of components in a given sample of a gaseous fuel. Thus, comparatively, an MIR analyzer detects only a selected set of species, in contrast to the full species characterization offered by an FTIR analyzer. However, an MIR analyzer has characteristics making onboard installation and use more feasible as contrasted with characteristics of an FTIR analyzer. The lower cost of MIR analyzer equipment makes installation and use more feasible for onboard detection, in particular, allowing for installation and use of a plurality of MIR analyzers on a given engine and/or on multiple engines at the site. MIR analyzer processes require relatively shorter detection time periods making the process more suitable for onboard detection functions as contrasted to FTIR analyzers, allowing for shorter feedback times as preferred in onboard applications. MIR analyzers are relatively less sensitive, as compared to FTIR analyzers, to temperature and vibrations in a manner that renders MIR analyzers more suitable for onboard installation and use.

A third stage of detection may be provided in some embodiments as an onboard exhaust gas stage, wherein characteristics of the natural gas fuel may be detected by reference to sensed characteristics of post-combustion exhaust gas emitted from at least one of the internal combustion engines of the system. The third stage is represented as lambda characterization step and sensor 106 in FIG. 1. The means for detection in the lambda characterization step or sensor 106 may comprise at least one analyzer or sensor positioned downstream of the engine block of at least one engine in the system, to detect characteristics of the post-combustion exhaust gas. The sensor 106 may preferably be at least one oxygen sensor that measures or estimates a net amount of oxygen in the exhaust gas. The oxygen sensor may chemically combine the oxygen and reductants in the exhaust gas, and then measure either the amount of remaining oxygen or the amount of oxygen required to consume the remaining reductants. Thus, the sensor generates values reflecting the measurement of oxygen. These values may be converted to a lambda scale comprising numbers greater than one for excess oxygen conditions and less than one for excess reductant conditions. The lambda values may be recorded.

As shown in FIG. 1, the detected characteristics and/or values representing the characteristics may be provided or communicated to a unit of the control system or processor of the system 100. The step or unit is represented as reference numeral 108 in FIG. 1. The unit 108 may comprise a data integration unit and a real-time estimator unit that generates values reflecting the detected characteristics of the natural gas fuel by interpreting and integrating detected information, which may be in the form of composition of the natural gas, its constituents or components, and species identification information and/or concentration values reported by the MIR analyzer 102, the FTIR analyzer 104, and/or the lambda sensor 106, and communicated to the unit 108 as shown by the arrows in FIG. 1. The unit 108 may interpret the values to generate signals comprising information on the composition and concentrations of species in the natural gas fuel being combusted in the engine on a real-time basis.

The information on the natural gas composition and species concentrations may include a pre-combustion air-to-fuel ratio (AFR) calculated by unit 108 in response to values reflecting the natural gas components and species concentrations values communicated by at least one of the MIR analyzer 102, the FTIR analyzer 104, and the lambda sensor 106. The information may include an AFR value that is communicated in a signal to an AFR/fuel feedback unit or step represented as AFR % fuel feedback 110 in FIG. 1. The AFR/fuel feedback unit or step may improve engine operation in response to the AFR value by controlling air intake levels and/or fuel intake levels to adjust the AFR to optimize engine performance on the basis of the real-time detected natural gas fuel characteristics.

In this manner, the embodiment yields an improved method and apparatus for real-time adjustment of AFR. The improvement may arise from combination of the enhanced detection of a larger range of types of species in the natural gas fuel as detected by the onsite FTIR analyzer, with the improved accuracy of concentration values detected onboard by the MIR analyzer at a time prior to but as close as possible to the time of combustion in the engine block.

The unit 108 may generate signals to a combustion referencing step or unit 112 of the control system. The signals may comprise information on the components and concentrations of species of components in the natural gas fuel being combusted. The signals may comprise information about the fuel being fed to the engine block, including, for example, a methane number (MN) of the fuel, a value indicating a tendency of the fuel to cause engine knock, or a lower heating value (LHV) of the fuel, a value reflecting an estimation of the amount of heat that will be released upon combustion of the fuel. The MN and/or LHV may be calculated by unit 108 in response to values reflecting the natural gas components and species concentrations values communicated by at least one of the MIR analyzer 102, the FTIR analyzer 104, and the lambda sensor 106.

The MN and/or LHV may be communicated in a signal to at least one of the combustion referencing step or unit 112 and the combustion limiting step or unit 114, as depicted by arrows in FIG. 1. The combustion limits step or unit 112 may generate control signals to control engine operation conditions or parameters in response to at least one of the MN or LHV. For example, the control signals may direct engine components to make adjustments to AFR ratios, lean/rich fueling parameters, or maximum brake torque (MBT) timing. In turn, signals output from the combustion referencing step or unit 112 to the combustion limiting step or unit 114, as depicted by arrows in FIG. 1, to provide further inputs to the combustion referencing functions.

The combustion referencing step or unit may improve engine operation in response to at least one of the communicated MN and LHV from the estimator unit 108 and communicated signals from the combustion limits unit 114, by controlling engine operating parameters to optimize engine performance on the basis of the real-time detected natural gas fuel characteristics. For example, the combustion referencing unit may interpret the MN or LHV, and/or inputs from the combustion limits unit 114, and, on the basis of the interpretation, generate control signals to control engine operating conditions or parameters such as AFR, cam phasing, exhaust gas lambda, or ignition timing. The control may improve engine performance under operating conditions, reduce engine knock, or enhance fuel efficiency. The control may improve engine performance in terms of observing combustion limits such as the maximum charge dilution that allows proper combustion in the given engine. Determination of the MN, and determining whether the MN will change, and if so, determining the timing of the change, may be useful to start limiting exhaust gas lambda characteristics before the effect is observed during combustion. Combustion limits may be used as inputs for engine reference managers.

In this manner, embodiments of the invention yield an improved method and apparatus for real-time adjustment of engine operating conditions and parameters. The improvement may arise from combination of the enhanced detection of a larger range of types of species in the natural gas fuel as detected by the onsite FTIR analyzer, with the improved accuracy of concentration values detected onboard by the MIR analyzer at a time prior to but as close as possible to the time of combustion in the engine block. This combination of detected values may further be combined with real-time lambda values detected by the lambda sensors in the exhaust gas to further improve engine operation as the result of improved detection of natural gas fuel characteristics.

Figure 2:
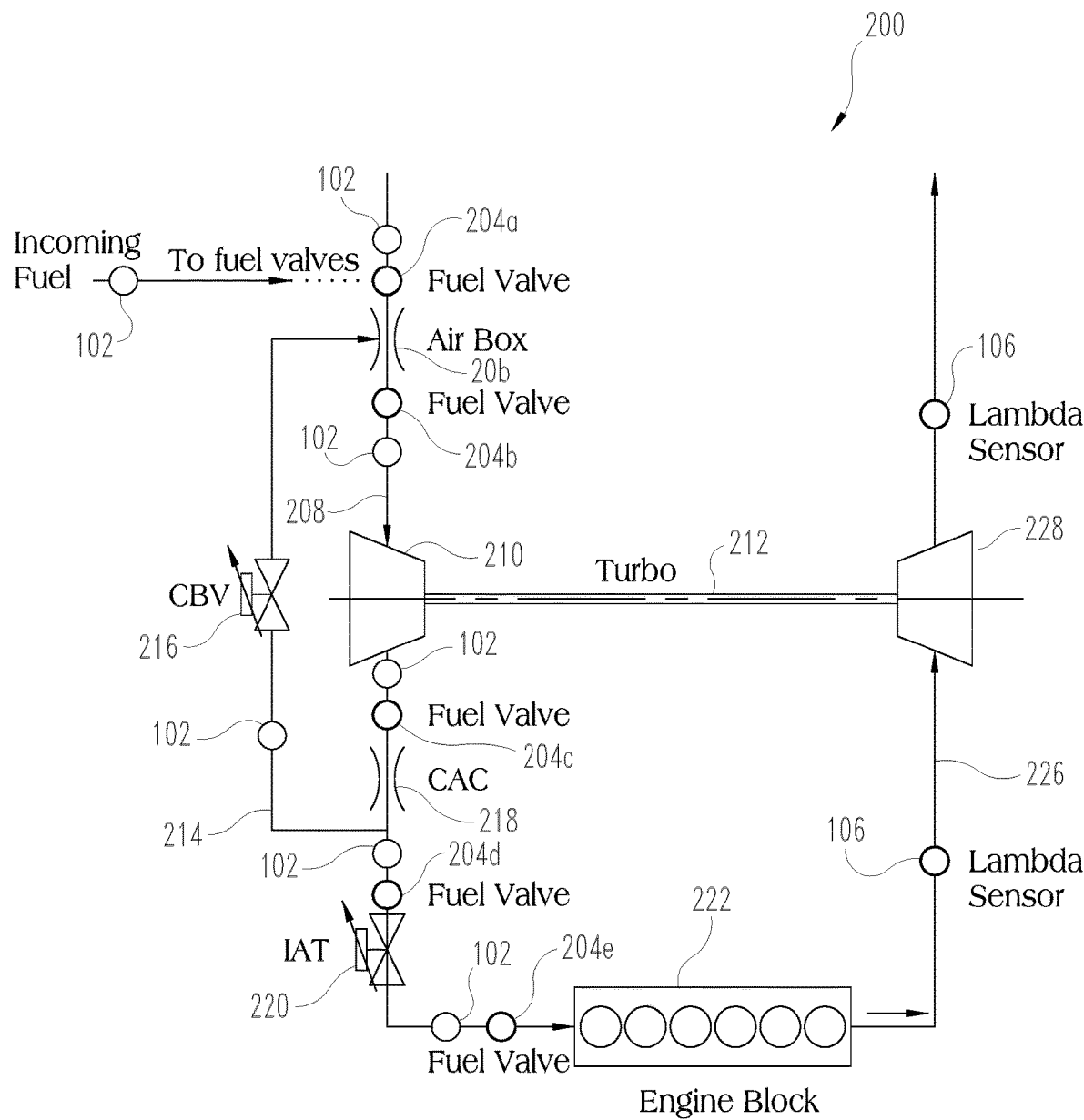
FIG. 2 is a schematic diagram representing an engine system according to some embodiments.

Embodiments of the invention include arrangements of MIR analyzers at different positions onboard the at least one internal combustion engine comprised in the engine system. FIG. 2 shows a schematic representation of an exemplary natural gas-fueled internal combustion engine system 200 of the inventive system. The engine system 200 may comprise MIR analyzers 102 disposed onboard the engine at one or more of a plurality of positions along the intake lines feeding natural gas to the engine, and along fuel lines feeding natural gas fuel to the engine block. The MIR analyzers may preferably be disposed before and after fuel valves 204a-204e along the fuel line.

As seen in FIG. 2, in embodiments, MIR analyzers 102 may be disposed upstream and downstream of an air box 206 in a fuel intake line 208. In embodiments, MIR analyzers 102 may be disposed in the fuel intake line 208 upstream and downstream of an inlet of a compressor 210 of a turbocharger unit 212. In embodiments, MIR analyzers 102 may be disposed in a compressor bypass line 214 upstream of a compressor bypass valve (CBV) 216 for measurement of natural gas fuel characteristics of fuel in the compressor bypass line 214. In embodiments, MIR analyzers 102 may be disposed in the fuel intake line 208 upstream and downstream of a charge air cooler 218. In embodiments, MIR analyzers 102 may be disposed in the fuel intake line 208 upstream and downstream of an inlet to the intake manifold, and/or an intake air temperature sensor 220. In embodiments, MIR analyzers 102 may be disposed in the fuel intake line 208 upstream of the engine block 222 wherein the fuel is combusted. As may be appreciated from the representation in FIG. 2, the MIR analyzers may preferably be positioned to sense gas characteristics both pre-mixture with charge air, and post-mixture with charge air.

In pre-mix fuel systems, the fuel introduction point is upstream of the intake runners of the engine. For example, an introduction point may be upstream of an inlet of a compressor, or upstream of a post charge air cooler. The further upstream the fuel introduction point is, the longer the time before the fuel will reach the exhaust stream. Hence, in traditional systems employing only exhaust gas lambda sensors, the bandwidth of the control loop is limited, and thus the system capability to maintain AFR within requirements may be lessened during transient operation. The inventors contemplate employing exhaust gas lambda sensors in combination with the MIR and/or FTIR analyzers as described to address such shortcomings.

Also as seen in FIG. 2, exhaust gas lambda sensors 106, 106 may be disposed in the exhaust gas line 226 downstream of the engine block 222 to detect, sense, or estimate oxygen content and/or lambda readings in the exhaust gas. The lambda sensors 106, 106 may be disposed upstream and/or downstream of a turbine unit 228 of a turbocharger unit 212. Although not depicted in FIG. 2, it is also contemplated that MIR analyzers 102 may be disposed along the exhaust gas line 226, although this position may have lesser benefit, because this positioning increases the measurement delay from the point of fuel introduction into the engine block 222.

Any one or all of the MIR analyzers 102 and the lambda sensors 106 may be operatively connected to or coupled with a controller or processor of the system to provide or communicate to the controller or processor, via an input or an input device, detected or estimated characteristics and/or values related to characteristics of the fuel or the exhaust gas. The controller or processor may be adapted to interpret the characteristics and/or values, and may be operatively coupled with an output or output device. The output or output device may be operatively connected or coupled to provide control commands to one or more units or components of the system or the engine based on the detected or estimated characteristics.

Figure 3:
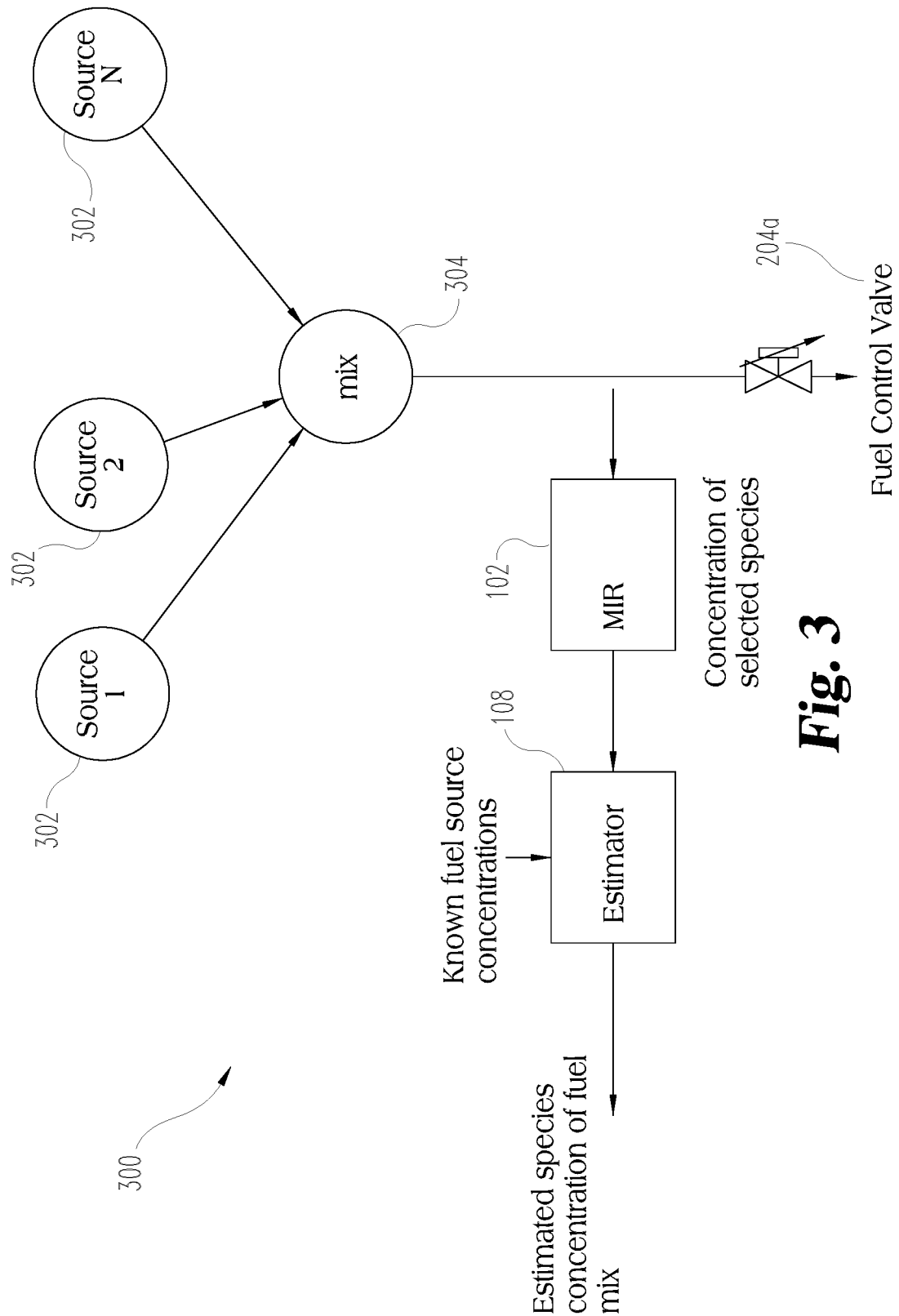
FIG. 3 is a schematic diagram representing a system or method for fuel characteristic determination according to some embodiments.

FIG. 3 is a schematic illustration of a system 300 for fuel characteristic determination under embodiments of the invention in a condition wherein natural gas fuel sources have relatively fixed or slowly changing properties. FIG. 3 may also represent steps of a method for such determination. As shown, fuel may be input from multiple fuel sources 302, 302. A step is conducted to assume or determine required species concentrations from each of the fuel sources. The assumption or determination might be a manual entry of known values, if the fuel characteristics from the fuel source in question are known to not change, or to change only slowly. Alternatively, the assumption or determination may be measured in real time using gas analyzers. In either case, the rate of change of the gas characteristics needs to be low enough that assumption or determination remains valid despite time lag needed for obtaining gas analyzer results and/or for system transport delay.

Another step may be conducted to measure the selected species concentrations at the sensor location downstream of a fuel mixer 304. The sensor location may preferably be at the position of the fuel control valve 204a positioned at or near a fuel inlet for an engine of the system. The measurement or estimation may be conducted using the onboard MIR analyzer 102. The species to be measured should be selected to allow proper calculation of all fuel fractions. When multiple fuel sources are present, a single species concentration measurement in this step might not be sufficient to uniquely determine the fraction of each fuel in the mix. And so a single species concentration measurement may limit the ability to accurately determine the species concentration of the resulting fuel mixture. In tur, this will limit the ability to determine MN and LHV of the resulting fuel mixture.

A calculation example is provided below for determination of mixture constituents.

Assume two fuel sources S1 and S2. Each fuel source is a composition including three constituents (A, B, and C).

Denote as follows:

$\mu_{A1}$, $\mu_{B1}$, $\mu_{C1}$ the mass fraction of constituent A, B and C, respectively, for source S1.

$\mu_{A2}$, $\mu_{B2}$, $\mu_{C2}$ the mass fraction of constituent A, B and C, respectively, for source S2

$\mu_{Am}$, $\mu_{Bm}$, $\mu_{Cm}$ the mass fraction of constituent A, B and C, respectively, for the mixture.

$W_1$, $W_2$, $W_m$ the mass flows for S1, S2 and the mixture respectively.

By definition, $$\mu_{Ci} = 1 - \mu_{Ci} - \mu_{Ci}, i \in \{1,2\}$$

$$W_m = W_1 + W_2$$

By conservation of mass, the mass fraction for the mixtures are $$\mu_{Am} = \frac{W_1 \mu_{A1} + W_2 \mu_{A2}}{W_1 + W_2}$$

$$\mu_{Bm} = \frac{W_1 \mu_{B1} + W_2 \mu_{B2}}{W_1 + W_2}$$

$$\mu_{Cm} = \frac{W_1 \mu_{C1} + W_2 \mu_{C2}}{W_1 + W_2}$$

$$\mu_{Cm} = 1 - \mu_{Am} - \mu_{Bm}$$

If the source constituents are known ($\mu_{A1}$, $\mu_{B1}$, $\mu_{C1}$, $\mu_{A2}$, $\mu_{B2}$, $\mu_{C2}$) as well as one constituent from the mixture ($\mu_{Am}$), there is a system of four equations and four unknowns ($W_1$, $W_2$, $\mu_{Bm}$, $\mu_{Cm}$) that can be solved to determine all the mixture constituents. With that one can calculate characteristics of the mixture such like MN. The calculation may be extended to more constituents. If more sources are present, the number of measured constituents of the mixture will need to be increased.

Further depicted in FIG. 3, another step may be conducted to use the fuel characterizations from the initial step above and the measured on-engine concentrations from the following step to infer fuel fractions from all the fuel sources. A further additional step is conducted to use source-based fuel characterizations from the initial step and the fuel fractions from the preceding step to calculate fuel mixture characterization including species concentration, MN, and LHV. The calculation may be conducted by an estimator unit 108 of the control system.

Figure 4:
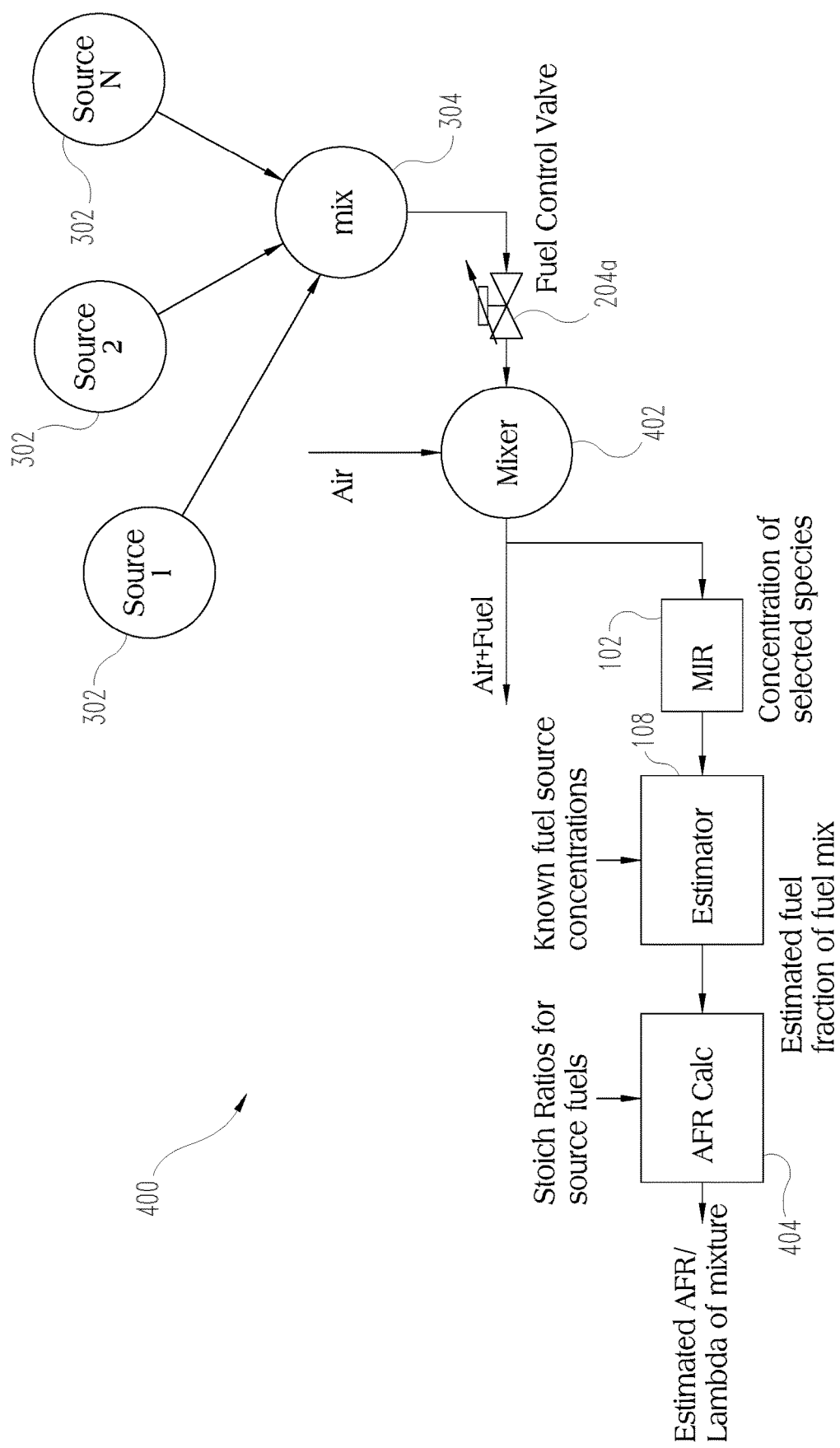
FIG. 4 is a schematic diagram representing a system or method for AFR determination according to some embodiments.

FIG. 4 is a schematic depiction of a system 400 for AFR determination under embodiments of the invention. FIG. 4 may also represent steps of a method for such determination. As shown, fuel may be input from multiple fuel sources 302, 302. An initial step is conducted to assume or determine required species concentrations from each of the fuel sources. Also conducted is an assumption or determination of required species concentrations of the air sources supplying the air to be used in the mixture with the fuel. Similarly to the system of FIG. 3, the assumption or determination might be a manual entry of known values, if the characteristics of the fuel from the source in question, or of the air from the source in question, are known to not change, or to change only slowly. Alternatively, the assumption or determination may be measured in real time using gas analyzers.

A further step is measurement of selected species concentrations at the location of at least one of the onboard MIR analyzers 102. With respect to the FIG. 4 system, where multiple fuel sources are present, species to be measured in the second step are to be selected as required to allow the calculation of AFR. When multiple fuel sources are present, a single specie concentration measurement in the second step might not be sufficient to uniquely determine the concentration of the remaining species. This will limit the ability to accurately determine AFR. The measurement may be conducted at a position downstream of an air/fuel mixer or mixing point 402 where air is introduced into the intake line and mixed with the natural gas fuel. AFR calculation based on MIR analyzer detection on the intake path (premix) enables faster fuel/lambda correction in the feedback control architecture. Concentrations of selected species are determined by at least one MIR analyzer 102 and communicated and input to an estimator unit 108, which makes a determination based on this input and the known/measured fuel source concentrations determined above.

A third step includes use of fuel compositions and air composition determinations from the first step, and using the mixture concentrations from the second step, to infer or determine to infer AFR. The estimator unit 108 determines and communicates an input to an AFR calculation unit 404 representing an estimated fuel fraction of the fuel mix. The AFR calculation unit 404 interprets this input together with an input of the stoichiometric rates of the source fuels. The AFR calculation unit 404 accordingly interprets these inputs to generate and communicate to the control system a value for the estimated AFR/lambda of the mixture.

A technique similar to that explained herein for fuel mixture composition calculation can be used by considering one of the sources to be air. Another simpler example is to consider a single known fuel source and air. Then, the MIR may be used to determine the concentration of one of the hydrocarbons (only present in the fuel). The ratio of concentrations of this hydrocarbon in the fuel and in the mixture is a direct indication of air fuel ratio as shown in the calculation example below.

Consider one fuel source S1 and Air. Fuel is a composition of two HC constituents (A,B). Air is C.

Denote as follows:

$\mu_{A1}$, $\mu_{B1}$, $\mu_{C1}$ the mass fraction of constituent A, B and C, respectively, for the fuel source S1.

$\mu_{A2}=0$, $\mu_{B2}=0$, $\mu_{C2}=1$ the mass fraction of constituent A, B and C, respectively, for air $\mu_{Am}$, $\mu_{Bm}$, $\mu_{Cm}$ the mass fraction of constituent A, B and C, respectively, for the air fuel mixture.

$W_1$, $W_2$, $W_m$ the mass flows for fuel, air and the mixture respectively.

By definition, $\mu_{Ci}=1-\mu_{Ci}-\mu_{Cp}$, $i \in \{1,2\}$ $$W_m = W_1 + W_2$$

By conservation of mass, the mass fraction for the mixtures are $$\mu_{Am} = \frac{W_1 \mu_{A1} + W_2 \mu_{A2}}{W_1 + W_2} = \frac{W_1 \mu_{A1}}{W_1 + W_2} \quad (1)$$

$$\mu_{Bm} = \frac{W_1 \mu_{B1} + W_2 \mu_{B2}}{W_1 + W_2} = \frac{W_1 \mu_{B1}}{W_1 + W_2} \quad (2)$$

$$\mu_{Cm} = \frac{W_1 \mu_{C1} + W_2 \mu_{C2}}{W_1 + W_2} = \frac{W_2 \mu_{C2}}{W_1 + W_2} \quad (3)$$

$$\mu_{Cm} = 1 - \mu_{Am} - \mu_{Bm} \quad (4)$$

Assume the source constituents are known ($\mu_{A1}$, $\mu_{B1}$, $\mu_{C1}$, $\mu_{A2}$, $\mu_{B2}$, $\mu_{C2}$) as well as one constituent from the mixture ($\mu_{Am}$). AFR is the ratio between air flow and fuel flow $W_2/W_1$. Applying Equation 1, we may calculate AFR by knowing the concentration of one fuel constituent in both the fuel source and in the mixture.

$$AFR = \frac{\mu_{Cm}}{\mu_{Am} + \mu_{Bm}} = \frac{\mu_{Cm}}{1 - \mu_{Cm}} = \frac{W_2 \mu_{C2}}{W_1 + W_2 - W_2 \mu_{C2}} = \frac{W_2}{W_1} = \frac{\mu_{Cm}(W_1 + W_2)/\mu_{C2}}{\mu_{Am}(W_1 + W_2)/\mu_{A1}}$$

In a fourth step under the system 400 of FIG. 4, in the case where multiple MIR analyzers 102 and lambda sensors 106 are available, a model is used to combine and interpret the information derived from the multiple analyzers and sensors. Due to differences in positions of the MIR analyzers 102, lambda sensors 106, analyzer response time, and sensing technology (MIR/O2 sensor), a dynamic model may be used to obtain an AFR estimate at the desired mixture location. A Kalman filter may be employed for obtaining the AFR estimate. In a simplified example of this step, assuming a single fuel source, B=CH₄ concentration in air at the fuel stoichiometric ratio; C=measured CH₄ in the air-fuel mixture; and the lambda estimation=B/C.

Figure 5:
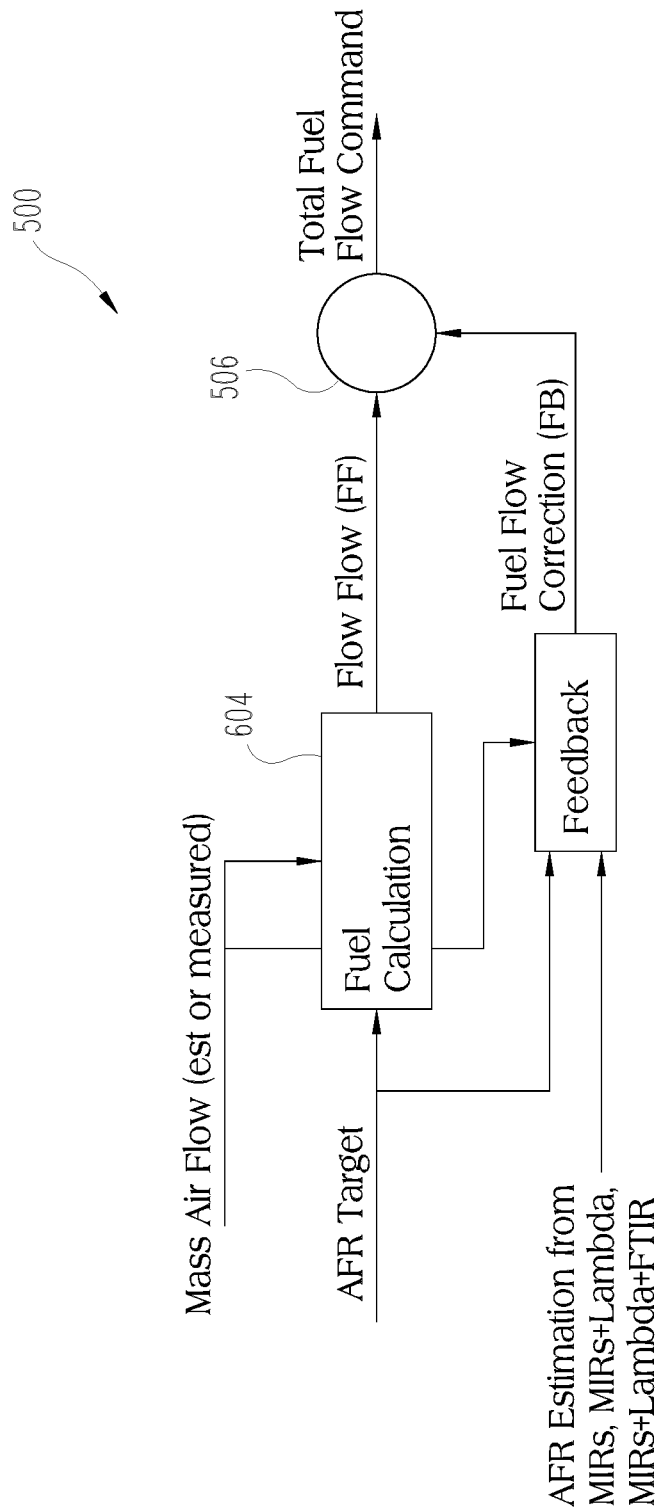
FIG. 5 is a schematic diagram representing a system for AFR control using features of some embodiments.

FIG. 5 provides a schematic representation of a system 500 for AFR control using features of embodiments of the invention. The representation also may represent steps in a method for AFR control in an engine of the system. Use of one or more MIR analyzers upstream of the power cylinders of the engine block 222 to estimate the mixture AFR is contemplated in order to accomplish faster and more accurate feedback control of AFR.

As shown in FIG. 5, the AFR estimation may be made on the basis of determinations from at least one of, or from a combination of one or more of, an MIR analyzer 102, an FTIR analyzer 104, and an exhaust lambda sensor 106 as described previously with respect to FIG. 1. The AFR estimation is input to a feedback unit 502 of a control system of the system. An AFR target input is also input into the feedback unit 502. The AFR target input is communicated to a fuel calculation unit 504 of a control system of the system.

A mass air flow input (estimated or measured) is communicated to the fuel calculation unit 504 and to the feedback unit 502. Based on the inputs of the AFR target and the mass air flow, the fuel calculation unit 504 determines a fuel flow value (FF). Based on the inputs of AFR target, mass air flow, and MIR analyzer 102, FTIR analyzer 104, and exhaust lambda sensor 106 as described previously, the feedback unit 502 determines a fuel flow correction value (FB). The determinations of the fuel calculation unit 504 and the feedback unit 502 are communicated to a total fuel flow command unit 506 that determines a value for a total fuel flow command.

The total fuel flow command may be communicated via outputs of the control system to components of the engine to set or adjust the total fuel flow. For example, the command may change spark timing (ST) as a function of the AFR condition as it actually exists in the cylinder, as opposed to as set in the target. Thus the MIR analyzer 102, FTIR analyzer 104, and/or lambda sensor 106 determinations are used in a feedback control command that enables a shorter feedback turnaround time. This is in contrast to prior systems wherein only readings from an exhaust sensor are employed to estimate mixture AFR.

Figure 6:
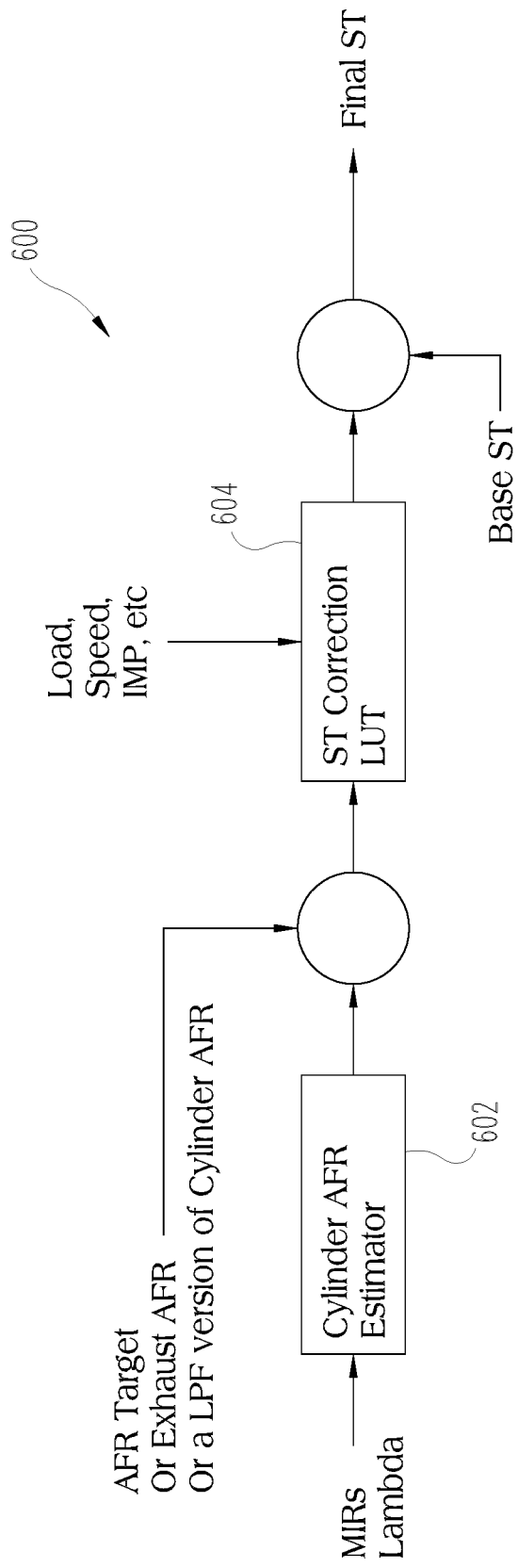
FIG. 6 is a schematic diagram representing a system for knock mitigation using features of some embodiments.

FIG. 6 is a schematic representation of a system 600 for knock mitigation under embodiments of the present invention. The representation also may represent steps in a method for knock mitigation controls in an engine of the system. Higher AFR controls bandwidths lessen the likelihood that AFR will remain on target during transient operations of the system. According to embodiments of the invention, benefits of the disclosed method and system for measuring or estimating AFR prior to the fuel reaching the combustion cylinder of the engine block 222 may include facilitating preventive measures such as: spark timing (ST) may be compensated to mitigate knock spikes in the case of rich deviations; or intake air throttle (IAT) may be adjusted to maintain better torque control. The torque model used to manipulate charge in response to a torque request can be enhanced by using estimated AFR obtained using embodiments of the system on a pre-combustion basis, for example, at the charge air cooler.

As seen in FIG. 6, a cylinder AFR estimation may be made by a cylinder AFR estimator unit 602 on the basis of determinations from at least one of, or from a combination of one or more of, an MIR analyzer 102, an FTIR analyzer 104, and an exhaust lambda sensor 106, as described previously with respect to FIG. 1. The cylinder AFR estimation is input to a spark timing (ST) correction unit (LUT) 604 of a control system of the system. Also input into the ST correction unit 604 are values for an AFR target, or exhaust AFR readings, or an LPF version of cylinder AFR. Also input into the ST correction unit 604 are values for load, speed, IMP, etc. engine control parameters. Based on such inputs, the ST correction unit 604 calculates and generates a value for a correction of the base ST to a final ST. Commands are issued by the control system to components of the engine system to implement the corrected ST.

There is disclosed herein: a method of operating an engine system, comprising determining a first characteristic of a natural gas fuel supplied to an engine of the system using a first analyzer disposed upstream of a fuel inlet of the engine; and determining a second characteristic of the fuel using a second analyzer disposed onboard the engine. The method may further comprise one, or more, or all of the following combinations or sub-combinations of features: controlling operation of the engine on the basis of the first and second characteristics; the first analyzer being a Fourier transform infrared analyzer; the second analyzer being a mid-infrared analyzer; the first characteristic being a concentration of at least two components of the fuel detected upstream of the fuel inlet; the second characteristic being a concentration of a component of the fuel detected onboard the engine; and/or comprising detecting oxygen content of exhaust gas of the engine, and controlling operation of the engine on the basis of the first and second characteristics and the oxygen content.

There is disclosed herein: a control system for a natural gas engine, comprising a processor coupled to an input and an output, wherein the input is adapted to receive a first characteristic of a natural gas fuel supplied to the engine, detected by a first analyzer disposed upstream of a fuel inlet of the engine, and a second characteristic of the fuel detected by a second analyzer disposed downstream of the fuel inlet, the output is adapted to provide a control command to the engine, and the processor is configured to determine a concentration of at least one component of the fuel based on the first and second characteristics, and provide the control command to the output based on the concentration. The control system may further comprise one, or more, or all of the following combinations or sub-combinations of features: the first analyzer being a Fourier transform infrared analyzer; the second analyzer being a mid-infrared analyzer; comprising a detector that detects a concentration of oxygen in exhaust gas of the engine; and/or the controller provides the control command to the output based on the concentration of the at least one component of the fuel and the concentration of oxygen in the exhaust gas.

There is disclosed herein, an engine system, comprising a natural gas engine; a mid-infrared analyzer disposed onboard the engine; and a controller coupled to the engine, the controller being configured to determine a concentration of at least one component of natural gas fuel supplied to the engine based on detection of components of the fuel by the mid-infrared analyzer and by a second analyzer disposed upstream of a fuel inlet of the engine, and to provide a control command to the engine based on the concentration. The engine system may further comprise one, or more, or all of the following combinations or sub-combinations of features: the second analyzer being a Fourier transform infrared analyzer; comprising a detector that detects a concentration of oxygen in exhaust gas of the engine; and/or the controller provides the control command based on the concentration of the at least one component of the fuel and the concentration of oxygen in the exhaust gas.

Many aspects of this disclosure are described in terms of sequences of actions to be performed by elements of a system, such as modules, a controller, a processor, a memory, and/or a computer system or other hardware capable of executing programmed instructions. Those of skill in the art will recognize that these elements can be embodied in an engine controller of an engine system, such as an engine control unit (ECU), also described as an engine control module (ECM), or in a controller separate from, and communicating with an ECU. In some embodiments, the engine controller can be part of a controller area network (CAN) in which the controller, sensor, actuators communicate via digital CAN messages. It will be recognized that in each of the embodiments, the various actions for implementing the regeneration optimization strategy disclosed herein could be performed by specialized circuits (e.g., discrete logic gates interconnected to perform a specialized function), by application-specific integrated circuits (ASICs), by program instructions (e.g. program modules) executed by one or more processors (e.g., a central processing unit (CPU) or microprocessor or a number of the same), or by a combination of circuits, instructions, and processors. All of which can be implemented in a hardware and/or software of the ECU and/or other controller or plural controllers.

Logic of embodiments consistent with the disclosure can be implemented with any type of appropriate hardware and/or software, with portions residing in the form of computer readable storage medium with a control algorithm recorded thereon such as the executable logic and instructions disclosed herein. The hardware or software may be on-board or distributed among on-board and off-board components operatively connected for communication. The hardware or software can be programmed to include one or more singular or multidimensional lookup tables and/or calibration parameters. The computer readable medium can comprise a random access memory (RAM), a read-only memory (ROM), an erasable programmable read-only memory (EPROM or Flash memory), an optical fiber, a portable compact disc read-only memory (CD-ROM), or any other solid-state, magnetic, and/or optical disk medium capable of storing information. Thus, various aspects can be embodied in many different forms, and all such forms are contemplated to be consistent with this disclosure.

One of skill in the art may appreciate from the foregoing that unexpected benefits are derived from application of the method, system, and apparatus to the problem of optimizing regeneration events in operating an engine system, without the need for additional components or parts, or changes in the configuration of a conventional vehicle or its features. Changes to configuration of a conventional engine system may add costs, weight, and complexity to manufacture, operation, and maintenance of the engine system. A key benefit contemplated by the inventors is improvement of control of regeneration events in a conventional engine system through use of the disclosed optimization system, method, or apparatus, while excluding any additional components, steps, or change in structural features. In this exclusion, maximum cost containment may be effected. Accordingly, the substantial benefits of simplicity of manufacture, operation, and maintenance of standard or conventionally produced vehicles as to which the method and system may be applied may reside in an embodiment of the invention consisting of or consisting essentially of features of the method, system, or apparatus disclosed herein. Thus, embodiments of the invention contemplate the exclusion of steps, features, parts, and components beyond those set forth herein. The inventors contemplate, in some embodiments, the exclusion of certain steps, features, parts, and components that are set forth in this disclosure even when such are identified as preferred or preferable.

It is to be understood that the above description is intended to be illustrative, and not restrictive. Many other embodiments will be apparent to those of skill in the art upon reading and understanding the above description. For example, it is contemplated that features described in association with one embodiment are optionally employed in addition or as an alternative to features described in association with another embodiment. The scope of the invention should, therefore, be determined with reference to the appended claims, along with the full scope of equivalents to which such claims are entitled.

The invention claimed is:

1. A method of operating an engine system, comprising:
    determining a first characteristic of a natural gas fuel supplied to a plurality of engines of the engine system using a first analyzer disposed upstream of a fuel inlet of each of the plurality of engines, wherein the first characteristic includes identification of a plurality of components of the natural gas fuel;

determining a second characteristic of the natural gas fuel using a second analyzer disposed onboard of one of the plurality of engines downstream of the fuel inlet to the one of the plurality of engines, wherein the second characteristic includes a concentration of one or more of the identified components of the natural gas fuel determined by the first analyzer;

determining a fuel flow value for the natural gas engine in response to an air-fuel ratio target and a mass air flow to the natural gas engine;

estimating an air-fuel ratio based on the identification of the plurality of components of the natural gas fuel from the first analyzer and the concentration of the one or more of the identified components of the natural gas fuel from the second analyzer;

determining a fuel flow correction value based on the fuel flow value and the estimate of the air-fuel ratio; and providing a total fuel flow command based on the fuel flow value and the fuel flow correction value.

2. The method of claim 1, comprising controlling operation of the one of the plurality of engines on the basis of the first and second characteristics.

3. The method of claim 1, wherein the first analyzer is a Fourier transform infrared analyzer.

4. The method of claim 1, wherein the second analyzer is a mid-infrared analyzer.

5. The method of claim 3, wherein the second analyzer is a mid-infrared analyzer.

6. The method of claim 1, comprising detecting oxygen content of exhaust gas of the one of the plurality of engines, and controlling operation of the one of the plurality of engines on the basis of the identification of the plurality of components of the natural gas fuel from the first analyzer and the concentration of the one or more of the identified components of the natural gas fuel determined by the second analyzer, and the oxygen content obtained from a detector disposed onboard the one of the plurality of engines.

7. A control system for a natural gas engine, comprising:

a processor coupled to an input and an output, wherein the input is adapted to receive a first characteristic of a natural gas fuel supplied to a plurality of natural gas engines, detected by a first analyzer disposed upstream of a fuel inlet of each of the plurality of natural gas engines wherein the first characteristic includes identification of a plurality of components of the natural gas fuel, and a second characteristic of the fuel detected by a second analyzer disposed downstream of the fuel inlet to the natural gas engine wherein the second characteristic includes a concentration of one or more of the identified components of the natural gas fuel determined by the first analyzer, the output is adapted to provide a control command to the natural gas engine, wherein the processor is configured to:

determine a fuel flow value for the natural gas engine in response to an air-fuel ratio target and a mass air flow to the natural gas engine;

estimate an air-fuel ratio based on the identification of the plurality of components of the natural gas fuel from the first analyzer and the concentration of the at least one of the plurality of components of the natural gas fuel from the mid-infrared analyzer;

determine a fuel flow correction value based on the fuel flow value and the estimate of the air-fuel ratio; and provide the control command to the output as a total fuel flow command based on the fuel flow value and the fuel flow correction value.

8. The control system of claim 7, wherein the first analyzer is a Fourier transform infrared analyzer.

9. The control system of claim 7, wherein the second analyzer is a mid-infrared analyzer.

10. The control system of claim 8, wherein the second analyzer is a mid-infrared analyzer.

11. The control system of claim 7, comprising a detector that detects a concentration of oxygen in exhaust gas of the natural gas engine.

12. The control system of claim 11, wherein the processor provides the control command to the output based on the concentration of the one or more identified components of the natural gas fuel and the concentration of oxygen in the exhaust gas.

13. An engine system, comprising:

a plurality of natural gas engines;

a first analyzer disposed upstream of a fuel inlet to each of the plurality of natural gas engines, the first analyzer being configured to identify a plurality of components of the natural gas fuel;

a mid-infrared analyzer disposed onboard one of the plurality of natural gas engines; and a controller coupled to the one of the plurality of natural gas engines, the controller being configured to determine a concentration of at least one of the plurality of identified components of the natural gas fuel supplied to the one of the plurality of natural gas engines based on detection of the concentration of one or more of the plurality of identified components of the natural gas fuel by the mid-infrared analyzer, and wherein the controller is configured to:

determine a fuel flow value for the one of the plurality of natural gas engines in response to an air-fuel ratio target and a mass air flow to the one of the plurality of natural gas engines;

estimate an air-fuel ratio based on the identification of the plurality of components of the natural gas fuel from the first analyzer and the concentration of the at least one of the plurality of components of the natural gas fuel from the mid-infrared analyzer;

determine a fuel flow correction value based on the fuel flow value and the estimate of the air-fuel ratio; and provide a control command to the one of the plurality of natural gas engines as a total fuel flow command based on the fuel flow value and the fuel flow correction value.

14. The engine system of claim 13, wherein the first analyzer is a Fourier transform infrared analyzer.

15. The engine system of claim 13, comprising a detector that detects a concentration of oxygen in exhaust gas of the at least one of the plurality of natural gas engines.

16. The engine system of claim 15, wherein the controller provides the control command based on the concentration of the at least one component of the natural gas fuel and the concentration of oxygen in the exhaust gas.

17. The engine system of claim 13, wherein the controller is configured to:

determine a pre-combustion air-fuel ratio based on the identification of the plurality of components of the natural gas fuel from the first analyzer and the concentration of the at least one of the plurality of components of the natural gas fuel from the mid-infrared analyzer; and adjust air intake and fuel levels to the one of the plurality of natural gas engines in response to the pre-combustion air-fuel ratio.

18. The engine system of claim 17, wherein the controller is configured to:

determine a methane number based on the identification of the plurality of components of the natural gas fuel from the first analyzer and the concentration of the at least one the plurality of components of the natural gas fuel from the mid-infrared analyzer; and adjust one or more combustion parameters of the one of the plurality of natural gas engines in response to the methane number.

\* \* \* \* \*